United States Patent
Schobben et al.

(10) Patent No.: US 11,878,178 B2
(45) Date of Patent: Jan. 23, 2024

(54) IMPLANTABLE MEDICAL DEVICE WITH TWO OR MORE ENCAPSULATED COMPONENTS

(71) Applicant: SALVIA BIOELECTRONICS B.V., Eindhoven (NL)

(72) Inventors: Daniel Schobben, Eindhoven (NL); Hubert Martens, Eindhoven (NL)

(73) Assignee: Salvia BioElectronics B.V., Eindhoven (NL)

( * ) Notice: Subject to any disclaimer, the term of this patent is extended or adjusted under 35 U.S.C. 154(b) by 240 days.

(21) Appl. No.: 17/312,406

(22) PCT Filed: Dec. 10, 2019

(86) PCT No.: PCT/IB2019/060625
§ 371 (c)(1),
(2) Date: Jun. 10, 2021

(87) PCT Pub. No.: WO2020/121198
PCT Pub. Date: Jun. 18, 2020

(65) Prior Publication Data
US 2022/0062649 A1    Mar. 3, 2022

(30) Foreign Application Priority Data

Dec. 10, 2018 (NL) .................................... 2022160

(51) Int. Cl.
*A61N 1/375* (2006.01)
*A61N 1/36* (2006.01)

(52) U.S. Cl.
CPC ......... *A61N 1/3756* (2013.01); *A61N 1/3605* (2013.01)

(58) Field of Classification Search
None
See application file for complete search history.

(56) References Cited

U.S. PATENT DOCUMENTS

| 8,831,747 | B1 | 9/2014 | Min et al. |
| 2008/0154365 | A1* | 6/2008 | Tai ............... B81C 1/00333 |
| | | | 257/E23.177 |

(Continued)

FOREIGN PATENT DOCUMENTS

| EP | 2230507 A1 | 9/2010 |
| WO | 2018111943 A1 | 6/2018 |

OTHER PUBLICATIONS

Search Report for International Patent Application PCT/IB2019/060625 dated Jun. 18, 2020.

*Primary Examiner* — Erica S Lee
*Assistant Examiner* — Elizabeth K So
(74) *Attorney, Agent, or Firm* — Fresh IP PLC; Clifford D. Hyra; Aubrey Y. Chen (57) ABSTRACT

Implants must protect against implant contamination and corrosion of electronics. However, when electrical components are fitted to flexible substrates, failure can occur at electrical connections.
An implant comprises: a flexible substrate; a first and second electrical component at a first and second position, electrically connected through an interconnect layer; a first and second component cover, separately encapsulating the first and second component to resist the ingress of body fluids into the component positions; wherein the flexible substrate allows a relative change in disposition between the first component cover and the second component cover. One or more electrodes are provided at a third position.
By encapsulating each component separately, the position of force/tension is moved away from the component attachment position to a point somewhere between the component positions. By disposing one or more electrode away from the components, the ingress is further restricted.

23 Claims, 8 Drawing Sheets

(56) References Cited

U.S. PATENT DOCUMENTS

| | | |
|---|---|---|
| 2009/0131995 A1 | 5/2009 | Sloan |
| 2010/0148345 A1* | 6/2010 | Eckhardt ............. H01L 23/4985 |
| | | 438/653 |
| 2012/0112347 A1* | 5/2012 | Eckhardt ................ H01L 24/24 |
| | | 257/751 |
| 2013/0334680 A1* | 12/2013 | Boone ............... H01L 23/49575 |
| | | 438/114 |
| 2017/0246459 A1 | 8/2017 | Kelley et al. |
| 2018/0339150 A1 | 11/2018 | Janik et al. |

* cited by examiner

IMPLANTABLE MEDICAL DEVICE WITH TWO OR MORE ENCAPSULATED COMPONENTS

FIELD

The present disclosure relates to an implantable medical device comprising a flexible substrate and two or more encapsulated components. In particular, it relates to an implantable medical device for neurostimulation, comprising one or more electrodes.

BACKGROUND

Implantable devices require a protection method, both to protect a human or animal body from implant contamination and to protect implant electrical connections and electronics from corrosion. Encapsulation is a critical component for the design of a medical device implant—it acts as a barrier between the active electronics and the inside of the human body. The function of this barrier is to prevent electrical current and materials leakage from the device into the body and to protect the electronics from human body fluids in order to prevent the degradation process of the implant electronics.

Currently, bulky feedthroughs and headers must be incorporated in the design of medical devices, such as implantable pulse generators (IPG), to reduce the risk of water ingress. The electronics are often packed into hermetic titanium cans or cases, which are bulky. This means that efforts to miniaturize such implantable devices are hindered.

Materials such as Liquid Crystal Polymers (LCP) are particularly suitable for implantable devices. Manufacturers combine thin film technology, as known from the semiconductor industry, with traditional flex circuit manufacturing technologies, to manufacture multilayer substrates that can assembled with standard Surface-Mount Technology (SMT) processes. This can reduce the thickness of the substrate and some electrical interconnections. However, when electrical components are fitted to these flexible substrates, failure can occur at the electrical connections.

US 2018/0339150A1 describes an electrode array with a flexible array substrate on which plural spaced apart electrodes are disposed. Integrated circuits are disposed in the array substrate. The integrated circuits are mounted to package substrates. The package substrates are more rigid than the array substrate. Internal to each package substrate is at least one electrical conductor. The electrical conductor extends from a bond pad integral with integrated circuit at least partially through the package substrate. The electrical conductor functions as the conductive member that extends between the integrated circuit an electrode with which the integrated circuit is associated.

EP 2 230 507A1 describes an environmental sensor comprising: a semiconductor die having a transducer provided on a surface thereof; a carrier substrate comprising electrical connections connected to the semiconductor die surface; and a layer of a sealing compound covering the semiconductor die surface and providing a seal between the die and the carrier substrate, wherein the transducer is configured to detect a change in an environmental parameter to which the sealing compound is exposed.

It is an object of the invention to provide improved implantable medical devices that are more reliable and to still retain their resistance to fluid ingress.

GENERAL STATEMENTS

According to a first aspect of the present disclosure, there is provided an implantable medical device comprising: a flexible substrate having one or more electrical interconnect layers interposed between a first flexible substrate layer and a second flexible substrate layer; a first electrical component disposed at a first component position; a second electrical component disposed at a second component position, the first and second component positions being disposed along a longitudinal axis; the first electrical component being electrically connected with the second electrical component through the one or more electrical interconnect layers; a first component cover, configured and arranged to encapsulate the first component and to resist the ingress of fluids from a human or animal body into the first component position; a second component cover, configured and arranged to separately encapsulate the second component and to resist the ingress of fluids from a human or animal body into the second component position; wherein the flexible substrate is further configured and arranged to allow a relative change in disposition between the first component cover and the second component cover; the device further comprising: a stimulation electrode, configured to transmit energy to human or animal tissue, disposed at a third component position further along the longitudinal axis from the first and/or second component positions; the stimulation electrode being electrically connected with the first and/or second electrical component through the one or more electrical interconnect layers.

By providing more than one component location, and encapsulating each component separately, the position of force/tension is moved away from the component attachment position to a point somewhere between the first and second component positions. This is also a point between the first and second component covers and/or the point where the first and/or second component covers are joined to the flexible substrate layer. The mechanical stress to which the component electrical attachment points are subjected may be reduced considerably. A plurality of component positions may be provided, allowing a high degree of flexibility in adapting the 3D-shape of the device along and/or around the longitudinal axis. In particular, the 3D-shape may approximate to the shape of an anatomical feature and/or structure against which it is implanted.

In addition, by having one or more electrodes, disposed away from the first and/or second component positions, the risk of fluid ingress may be further reduced.

This ingress is a potential risk with the known devices described in US2018/0339150A1, where the electrodes and ASIC's are disposed at substantially the same longitudinal position. Any interface between a substrate material (such as a parylene shell) and conductive electrode material may provide an additional ingress path for fluids to reach the ASIC's. Such devices are very sensitive to corrosion, and may quickly malfunction or perform less optimally. By positioning one or more electrodes away from the electrical components, fewer and/or longer ingress paths are available for fluids to reach the electrical components. In other words, the ingress path for fluids is further restricted.

According to a further aspect of the current disclosure, there is provided an implantable medical device, wherein the change in disposition comprises: a change in separation along the longitudinal axis between the first component cover and the second component cover; a change in rotation about a transverse axis disposed between the first component cover and the second component cover, the transverse axis being substantially perpendicular to the longitudinal axis; a change in rotation about the longitudinal axis; and any combination thereof.

A change in separation allows a shrinking or a stretching over the longitudinal length. A change in rotation about a first transverse axis, which may also be described as a change in pitch, allows the medical device to adopt a more circular cross-section. A change in rotation about a second transverse axis, which may also be described as a change in yaw, allows the medical device to adopt meanders along the longitudinal axis. A change in rotation about the longitudinal axis, which may also be described as a change in roll, allows the medical device to adopt a corkscrew-like profile along the longitudinal axis. One or more of these changes may improve the accuracy with which the 3D-shape approximates the shape of an anatomical feature and/or structure against which it is implanted.

According to a further aspect of the current disclosure, there is provided an implantable medical device, wherein the device comprises a Liquid Crystal Polymer (LCP) and/or a Polyimide in one or more of the following: the first flexible substrate layer; the second flexible substrate layer; the first component cover; the second component cover; and any combination thereof.

Liquid Crystal Polymers (LCP) are chemically and biologically stable thermoplastic polymers which allows for hermetic sensor modules having a small size and low moisture penetration. Advantageously, LCP can be thermoformed allowing component covers with complex shapes to be provided.

According to another aspect of the current disclosure, there is provided an implantable medical device which further comprises: a third electrical component disposed at a third component position; the third electrical component being electrically connected with the first and/or second electrical component through the one or more electrical interconnect layers; the third electrical component being: a stimulation electrode configured to transmit energy to human or animal tissue; and/or a sensor configured to detect a presence of an environmental property in human or animal tissue.

For neurostimulation, one or more electrodes may be provided, using the one or more electrical interconnect layers (or a further interconnect layer) for electrical connections to the first and/or second electrical component. Additionally or alternatively, one or more sensors may be provided, allowing direct measurements of parameters relevant for operation, such as humidity, temperature, electrical resistance and electrical activity.

According to yet another aspect of the current disclosure, there is provided an implantable medical device wherein the first component position and/or second component position further comprises a fluid detector, encapsulated by respectively the first component cover or the second component cover.

Protecting against fluid ingress is critical for implantable devices. In spite of using optimal materials and processes, a degree of ingress may occur. In addition, particularly when using flexible substrates, defects may occur after a period of time allowing some fluid to penetrate into the component position. It is therefore particularly advantageous to provide a fluid sensor at a component positions, within the encapsulation.

According to a further aspect of the current disclosure, there is provided an implantable medical device wherein a first fluid detector at the first component position is electrically connected to a second fluid detector at the second component position through the one or more electrical interconnect layers.

Additionally or alternatively, a single fluid detector may be electrically connected to more than one electrical component, reducing the need to provide a fluid detector within the encapsulation of each component position.

According to a still further aspect of the current disclosure, there is provided an implantable medical device wherein the fluid detector comprises two or more electrical conductors, substantially equidistant electrical conductors over at least part of their extent.

A relatively simple fluid detector may be provided using two or more equidistant conductors, such as a portion with substantially parallel electrical conductors.

According to another aspect of the current disclosure, there is provided an implantable medical device wherein: the first electrical component and/or second electrical component have substantially larger dimensions along a transverse axis than along the longitudinal axis.

By providing rectangular components with a high length-to-width ratio, a higher degree of bending (rotation around a transverse axis) may be achieved. This may also reduce the length of the implant along the longitudinal axis.

Additionally or alternatively, the component covers may have substantially larger dimensions along a transverse axis than along the longitudinal axis. In other words, one or more covers may have a high length-to-width ratio. Preferably, each cover is dimensioned to provide substantially equal degree of encapsulation around the component, so the cover may have similar dimensions (and shapes/forms) as the components.

According to yet another aspect of the current disclosure, there is provided an implantable medical device wherein the first component position and/or second component position comprises a plurality of electrical components, electrically connected to each other with the one or more electrical interconnect layers, and encapsulated by respectively the first component cover or the second component cover.

Advantageously, one or more of the component positions may comprise a further component within the encapsulation. This may provide additional design flexibility allowing, for example, both analog and digital functionality, or memory and processing, at a single component position. In some cases, this may also reduce the longitudinal extent of the device as it is not required to comprise the further component at a further component position, with a further component cover, configured and arranged to encapsulate the further component, and to resist the ingress of fluids from a human or animal body into the further component position.

BRIEF DESCRIPTION OF THE DRAWINGS

Features and advantages of some embodiments of the present invention, and the manner in which the same are accomplished, will become more readily apparent upon consideration of the following detailed description of the invention taken in conjunction with the accompanying drawings, which illustrate preferred and exemplary embodiments, and which are not necessarily drawn to scale, wherein.

DETAILED DESCRIPTION

In the following detailed description, numerous non-limiting specific details are given to assist in understanding this disclosure. It will be obvious to a person skilled in the art that the software methods may be implemented on any type of suitable controllers, memory elements, and/or computer processors.

Figure 1A:
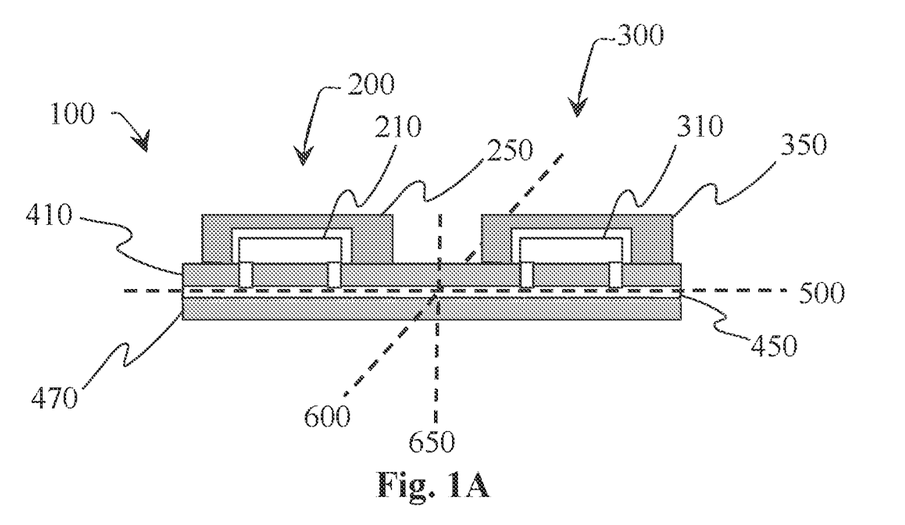
FIG. 1A depicts a longitudinal cross-section and FIG. 1B depicts a transverse surface of an improved implantable device.

FIG. 1A depicts a longitudinal cross-section through an improved implantable device 100. It comprises:
- a flexible substrate having one or more electrical interconnect layers 450 between a first flexible substrate layer 410 and a second flexible substrate layer 470. This is also known as a multilayer substrate. The multi-layer foil PCB disclosed in PCT application WO 97/18695 is suitable for this purpose;
- a first electrical component 210 disposed at a first component position 200;
- a second electrical component 310 disposed at a second component position 300, the first 200 and second 300 component positions being disposed along a longitudinal axis 500. As the substrate is flexible, this axis is not necessarily a straight line when in use, but it is depicted in a first orientation where the 3D-shape approximates the shape of a substantially flat surface against which it has been placed;
- the first electrical component 210 being electrically connected with the second electrical component 310 through the one or more electrical interconnect layers 450;
- a first component cover 250, configured and arranged to encapsulate the first component 210 and to resist the ingress of fluids from a human or animal body into the first component position 200; and
- a second component cover 350, configured and arranged to encapsulate the second component 310 and to resist the ingress of fluids from a human or animal body into the second component position 300.

The flexible substrate is further configured and arranged to allow a relative change in disposition between the first component cover 250 and the second component cover 350.

A first transverse axis 600 is depicted, which is substantially perpendicular to the longitudinal axis 500, and has the direction going into the paper (as depicted).

A second transverse axis 650 is also depicted, which is also substantially perpendicular to the longitudinal axis 500. In this example, the layers form a stack (a plurality of layers) at each component position 200, 300, the stack being disposed along the second transverse axis 600 in the following order:
- second flexible substrate layer 470;
- one or more electrical interconnect layers 450;
- first flexible substrate layer 410;
- a first 210 or second 310 electrical component; and optionally:
  - at the first component position 200, a first 250 component cover;
  - at the second component position 300, a second 350 component cover.

In FIG. 1A, the cross-section depicted lies in the plane comprising the longitudinal axis 500 and the second transverse axis 650. The electrical connections between each component 210, 310 and the one or more electrical interconnection layer 450 are depicted very schematically—there may be one or more through connections as depicted, or a single through connection. In some cases, a capacitive or inductive coupling may also be used.

The second flexible substrate layer 470 is configured and arranged to contact, after implantation, with an anatomical feature and/or structure. As the improved device is flexible and configured to allow a relative change in disposition, the 3D-shape of the device is configured and arranged to approximate to the shape of the anatomical feature and/or structure against which it is implanted. In particular, by providing two or more component positions 200, 300 and a relative change in disposition between the respective component covers means that the 3D-shape is approximated to a high degree along the longitudinal axis 500.

Figure 1B:
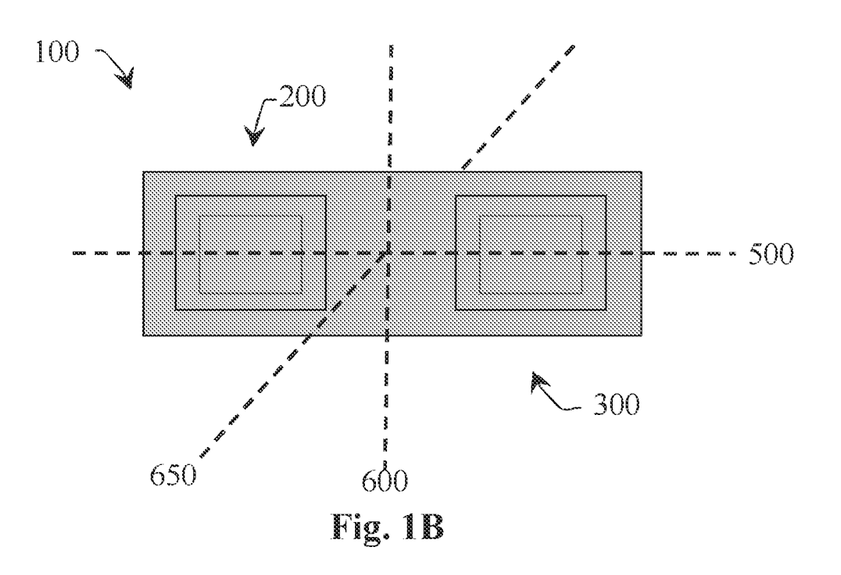

FIG. 1B depicts a perspective view of the first flexible layer 410 and the first 250 and second 350 component covers viewed from the side facing away, in use, from the anatomical feature and/or structure against which it is implanted.

In FIG. 1B, the side depicted lies in the plane comprising the longitudinal axis 500 and the first transverse axis 600.

Traditional implantable devices comprise one or more electrical components, encapsulated at one component position. One of the insights on which the invention is based is that separating the electrical components into separate component positions 200, 300, each with its own encapsulation 250, 350, greatly increases the ability of the implantable device to approximate its 3D-shape. particularly if the component positions 200, 300 are disposed along the longitudinal axis 50. As the dimensions of the components 210, 310, increase, typically related to the complexity of the functions they are to perform, separating the components 210, 310 into separate encapsulated component positions 200, 300, becomes more advantageous. To perform more complex functions, typically one or more electronic and/or active components 210, 310 are used.

An electronic component is a type of electrical component which uses electricity to manipulate information. An electronic component, such as a transistor or an integrated circuit comprises at least one active component.

An integrated circuit (or IC, chip, or microchip) is a component which comprises a plurality (or multiplicity) of electronic devices (or circuits) on a piece (or "chip") of semiconductor material. The plurality of devices are usually manufactured substantially simultaneously. The devices are connected together using one or more conductor which are also manufactured substantially simultaneously. For example, an integrated circuit component may be an application-specific integrated circuit ASIC, a field-programmable gate array FPGA, a surface-mount device SMD, a through-hole package, a chip carrier, a pin grid array, a flat package, a small outline package, a chip scale package, a ball grid array, a small-pin-count package.

A non-integrated circuit (or discrete circuit) comprises one or more discrete (or separate) electrical or electronic components. They are usually manufactured substantially separately. In the case of two or more discrete components, they are connected together using one or more conductors which are also manufactured substantially separately. For example, a discrete component may be an active component, a passive component, an electronic component, an analog component, a digital component, a surface-mount device SMD, a flexible silicon device, a thin-film transistor TFT.

An active component is an electrical component that is configured to control electron flow, such as a transistor, a rectifier, a diode. A passive component is an electrical component that is not configured to control electron flow, such as a resistor, a capacitor, an inductor, an electrode, a fluid sensor.

A further advantage to separate encapsulated component positions 200, 300 is that the encapsulation may be configured to take into account the physical and electrical properties of the encapsulated components 210, 310. For example, during operation, analog components 210, 310 may use higher voltages and/or currents than digital components 210, 310.

A further insights that provided an inspiration for this invention is that configuring and arranging the implantable device 100 to allow a relative disposition between the component covers 250, 350, the stress points are moved away from the electrical attachment points to one or more points between the covers 250, 350 where the flexible substrate 410, 430 allow relative movement. This greatly improves the reliability of the implantable medical device 100.

Flexible means that the substrate 410, 430 is able to be bent, turned or forced from a straight line without breaking when the relative change in disposition takes place. The one or more electrical interconnect layers 450 is also configured and arranged to be flexible.

Preferably, the flexible substrate 410, 430 is also resilient—in other words, it is able to spring back into shape and/or position after the force used to create the relative disposition has been removed or reduced.

The degree of flexibility of the substrate 410, 450, 470 between the covers 250, 350 may be configured and arranged by one or more of the following:
  selection of a suitable substrate material. Preferably a single substrate material is used, such as LCP or polyimide. However, the skilled person will realize that different materials may be used for different elements of the device, and composite materials are also possible. Additives, such as plasticizers, may also be added;
  selection of a suitable substrate thickness (extent along the second transverse axis 650);
  selection of a suitable width (extent along the first transverse axis 600)— although the drawings depict the substrate between the covers 250, 350 to be the same width, this is not required. The width may be less to permit a higher degree of relative disposition;
  making recesses or openings in the substrate 410, 450, 470 between the covers 250, 350.

Two component positions 200, 300 are depicted in FIGS. 1A and 1B, disposed along the longitudinal axis 500 with a separation between their respective component covers 250, 350. More than two encapsulated component positions may also be provided, either being disposed further along the longitudinal axis 500, and/or being disposed along the first transverse axis 600 and/or being disposed along the second transverse axis 600. In other words, 2D-arrays or 3D-arrays of encapsulated component positions may be provided.

Typically, the separation between oppositely-facing edges of the component covers 250, 350 may be in the range 0.1 mm to 10 mm. However, as it may be advantageous to keep the overall dimensions of implantable device 100 as small as possible, a separation of 2 mm is most preferred.

The extent of a component 210, 310 along the longitudinal axis 500 depends on the type of component used and how it is packaged. For example:
  an 8-pin dual inline package (DIP) typically has a width (including leads) of approximately 8 mm;
  a 32-pin DIP typically has a width (including leads) of approximately 15.5 mm;
  a mini small outline package (MSOP) typically has a width (including leads) of approximately 5 mm;
  a small outline transistor (SOT) typically has a width (including leads) of approximately 3 mm.

As the width of the component 210, 310 at least partially determines the overall extent along the longitudinal axis 500 of the device 100, it may be advantageous to use the smallest package possible. For example:
  surface mount device (SMD) passive components, such as resistors and capacitors typically have widths of approximately 0.15 mm to 6.5 mm;
  an SMD small outline transistor (SOT) package typically have widths of approximately 1 mm to 2 mm;
  an SMD narrow small outline integrated circuit (SOIP) with 8-pins may have a width (including leads) of typically approximately 6 mm;
  some ASIC's are available in packages which are only 1 mm wide.

As the components 210, 310 are encapsulated using the component covers 250, 350, bare chips (without a package) may also be used.

The cover 250, 350 is typically dimensioned to be larger than the dimensions of the component 210, 310 being encapsulated to provide a high degree of resistance to fluid ingress. For example, a perimeter of 300 microns (um) may be provided on one or more sides of the component 210, 310.

Depending on the extent of the component 210, 310 along the longitudinal axis 500, the extent of the respective cover may be in the range 1 mm to 10 mm. Preferably 2 mm is used.

Similarly, the extent along the second transverse axis 650 depends on the dimensions of the components used, the thickness of the substrate layers 410, 470, any additional extent of the one or more electrical interconnect layers 450, and the thickness of the cover 250, 350.
  typically, the cover 250, 350 thickness will be in the range 50 microns (um) to 500 microns (um), preferably 100 microns (um) to 300 microns (um).
  SMD components are available in packages, such as narrow SOIC, with thicknesses in the range approximately 1.5 mm to 2.5 mm. If required, standard packaging may be etched to make it thinner—for example ASIC's are available in thicknesses of approximately 0.1 to 0.2 mm.

The flexible substrate is configured and arranged to allow a relative change in disposition (movement) between the first component cover 250 and the second component cover 350. This allows a high degree of flexibility in adapting the 3-D shape of the device 100 along and/or around the longitudinal axis 500. In particular, the 3D-shape of the device 100 may approximate to the shape of an anatomical feature and/or structure against which it is implanted.

The flexibility is due to the dimensioning of the device 100 elements, as well as the selection of a suitable material.

For example, the device 100 may comprises a Liquid Crystal Polymer (LCP) and/or a Polyimide in one or more of the device elements. In particular, in the first flexible substrate layer 410; the second flexible substrate layer 470; the first component cover 250; the second component cover 350; and any combination thereof.

For example, flexible substrate materials produced by Dyconex AG may be used (www.mst.com/dyconex). LCP or Polyimide, for example.

Liquid Crystal Polymers (LCP) are chemically and biologically stable thermoplastic polymers which allows for hermetic sensor modules having a small size and low moisture penetration. Advantageously, LCP may be thermoformed allowing component covers with complex shapes to be provided.

At room temperature, thin LCP films have mechanical properties similar to steel. This is important as implantable devices 100 must be strong enough to be implanted, strong enough to be removed and strong enough to follow any movement of the anatomical feature and/or structure against which it is implanted.

LCP belongs to the polymer materials with the lowest permeability for gases and water. LCP can be bonded to itself, allowing multilayer constructions with a homogenous structure.

|  | Unit | LCP Flex | Polyimide Flex |
| --- | --- | --- | --- |
| Thickness | Um (micron) | 25, 50, 100 | 12, 25, 50 |
| Dielectric constant (10 GHz) | — | 2.9 | 3.2 |
| Dissipation factor (10 GHz) | — | 0.002 | 0.002 |
| Surface resistivity | ohm | 1.0 E16 | 4.0 E13 |
| Volume resistivity | Ohm cm | 1.0 E18 | 2.6 E14 |
| Dielectric strength | kV/mil | 3.5 | 7 |
| Young's modulus | GPa | 2.3 | 7.1 |
| Tensile strength | MPa | 280 | 220 |
| CTE, x-y | ppm/K | 18 | 20 |
| CTE, z | ppm/K | 200 | 120 |
| Solder float temperature | ° C. | >288 | >300 |
| Melting temperature/ glass transition | ° C. | 330 | 343 |
| Moisture absorption (23° C., 24 h) | % | 0.04 | 1 |
| Flammability | — | UL 94 VTM-0 | UL 94 V0 |

This table compares the properties of LCP with Polyimide. In contrast to LCP, polyimides are thermoset polymers, which require adhesives for the construction of multilayer substrates. Polyimides are thermoset polymer material with high temperature and flexural endurance.

LCP may be used, for example, to provide multilayers 410, 470 with several layers of 25 um (micron) thickness. The one or more electrical interconnect layers 450 may be provided by metallization using techniques from the PCB industry, such as metallization with copper. Electro-plating may be used.

The change in disposition may comprise:

a change in separation along the longitudinal axis between the first component cover 250 and the second component cover 350;

a change in rotation about a transverse axis 600, 650 disposed between the first component cover 250 and the second component cover 350, the transverse axis 600 being substantially perpendicular to the longitudinal axis 500;

a change in rotation about the longitudinal axis 500; and any combination thereof.

A change in separation allows a shrinking or a stretching over the longitudinal axis 500. A change in rotation about the first transverse axis 600, which may also be described as a change in pitch, allows the device 100 to adopt a more circular longitudinal cross-section. A change in rotation about the second transverse axis 650, which may also be described as a change in yaw, allows the device 100 to adopt meanders along the longitudinal axis 500. A change in rotation about the longitudinal axis 500, which may also be described as a change in roll, allows the device 100 to adopt a corkscrew-like profile along the longitudinal axis 500. One or more of these changes, in any combination, may improve the accuracy with which the 3D-shape approximates the shape of an anatomical feature and/or structure against which it is implanted.

Figure 2A:
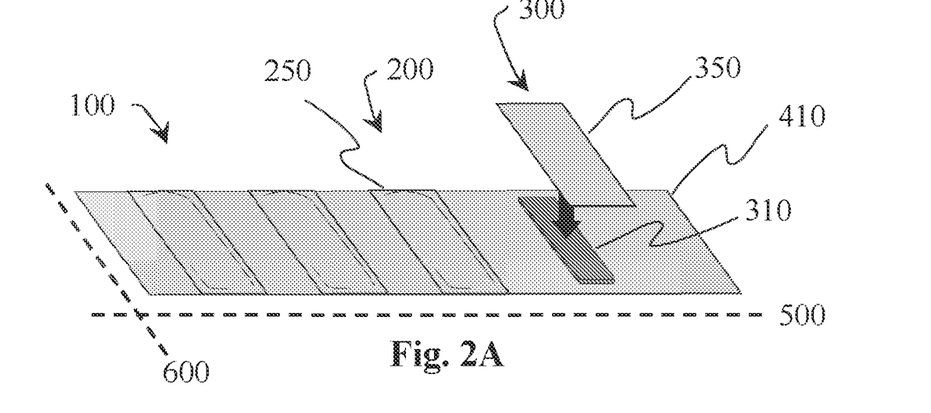
FIG. 2A depicts an improved implantable device having a plurality of encapsulated component positions.

FIG. 2A shows an improved implantable device 100 having a plurality of encapsulated component positions. It depicts a perspective view of the first flexible layer 410 and the first 250 and second 350 component covers viewed from the side facing away, in use, from the anatomical feature and/or structure against which the device is implanted. This side lies in a plane comprising the longitudinal axis 500 and the first transvers axis 600.

The first encapsulated component position 200 comprises the first electrical component 210 (not shown) which has already been encapsulated by providing the first component cover 250. At the second component position 300, the second electrical component 310 is provided on an outer surface of the first flexible layer 410 on the side facing away, in use, from the anatomical feature and/or structure against which the device is implanted The second component cover 350 is provided as a separate piece comprising a flexible material, such as LCP. The second component cover 350 is then configured and arranged to encapsulate the second electronic device 310—for example, if using a material such as LCP, the second cover 350 may be heat welded. Additionally, a frame (not shown) may also be provided around the second electrical component 310—a frame is particularly advantageous if the electrical component 310 to be encapsulated is relatively thick. Such a frame may also comprise a flexible material, such as LCP. An adhesive may also be used. Additionally or alternatively, conductors (wires) may be provided around the perimeter of the second cover 350, through which a suitable current may be passed to the second cover 350 to heat seal the cover 350.

Figure 2B:
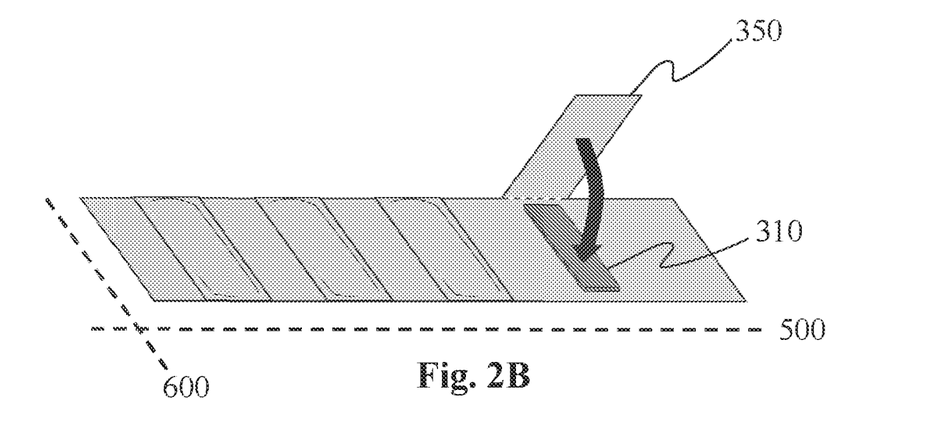
FIG. 2B depicts a perspective view of the first flexible layer and the first and second component covers.

FIG. 2B also depicts a perspective view of the first flexible layer 410 and the first 250 and second 350 component covers. It shows an alternative method for providing the second component cover 350—in this case, the cover 350 is rotationally attached to the first flexible layer 410 along a longitudinal edge. This may be advantageous as it speeds up the alignment of the cover to the electrical component 310 prior to completing the encapsulation. Similarly attachment using one or two corners is advantageous, as well as attaching along a transverse edge. The encapsulation is completed as described above for FIG. 2A using, for example, heat-sealing and/or an adhesive.

Figure 2C:
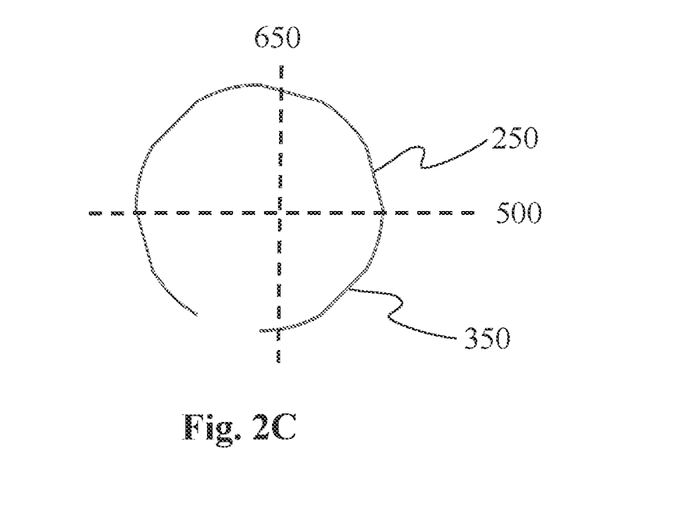
FIG. 2C depicts schematically a longitudinal cross-section, showing possible rotations about the first transverse axis.

FIG. 2C depicts schematically a longitudinal cross-section in the plane comprising the longitudinal axis 500 and the second transverse axis 650, showing possible rotations about the first transverse axis 600 (bend-points). Note that the first 200 and second 300 component positions are relatively flat, and the flexible substrate 410, 450, 470 is configured to allow the majority of the bending to occur substantially between the first 250 and second 350 covers. The region of maximum bend is the region of highest force/tension in the substrate 410, 450, 470—by suitable dimensioning, it is possible to provide the maximum bend substantially midway between the edge of the first cover 250 and the edge of the second cover 350. Other changes in separation may also be provided (not depicted).

FIG. 2C depicts an extreme example, which may be required if the anatomical feature and/or structure against which the device 100 is to be implanted is substantially circular in cross-section. In most applications, a reduced degree of bending will be sufficient for the 3D-shape to approximate the anatomical feature and/or structure.

A high degree of flexibility is provided by providing a plurality of relatively small (in the longitudinal direction 500) electrical component positions 200, 300 and component covers 250, 350. In other words, when viewed in longitudinal cross-section (similar to the situation depicted in FIG. 2C), the implantable device 100 comprises a plurality of relatively flat sections with a plurality of bends. This allows the implantable device 100 to form a relatively tight-fitting circle. This advantage may be further improved by providing electrical components with substantially larger dimensions along a transverse axis 600, 650 than along the longitudinal axis 500—in other words, with a high length-to-width ratio or rectangular integrated circuits. ASIC's are, for example, available with a 10:1 aspect ratio.

In general, covers are provided with the same length-to-width ratio and the same cross-sectional shape in a plane approximately parallel to a plane comprising the first substrate layer 410. Both the electrical components and covers may have any suitable transverse cross-sectional shapes, such as: circular, oval, elliptical, square, rectangular, trapezoidal. Alternatively, electrical components and covers have different cross-sectional shapes—however, to resist the ingress of bodily fluid, each cover should be substantially larger than the electrical component being encapsulated.

Figure 3A:
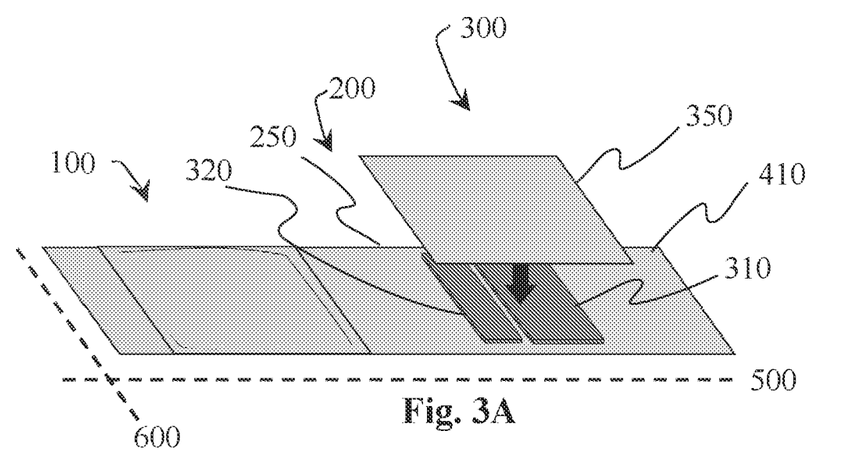
FIGS. 3A, 3B, and 3C depict further embodiments of the improved device.
Figure 3B:
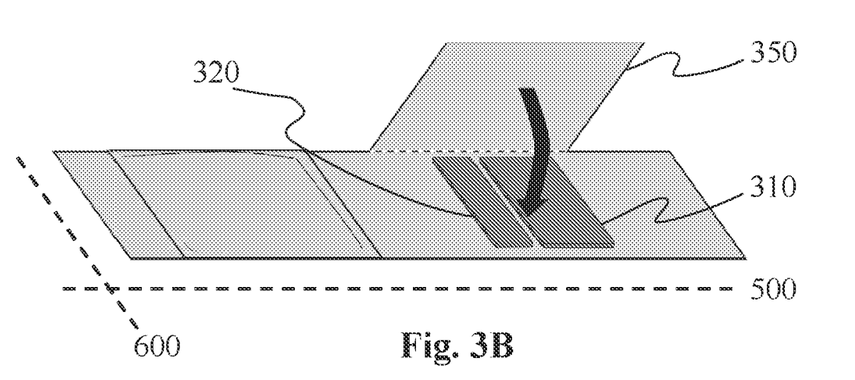
Figure 3C:
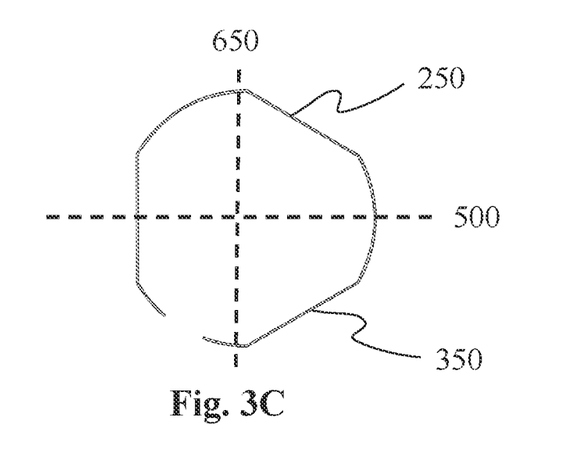

FIGS. 3A, 3B, and 3C depict further embodiments which are very similar to FIGS. 2A, 2B and 2C. FIG. 3A also depicts an improved implantable device 100 having a plurality of component positions. At the second component position 300, the second electrical component 310 is provided on the same outer surface of the flexible surface. In this case, a further component 320 is also provided on the outer surface of the first flexible layer 410. The further component 320 is also electrically connected with the one or more electrical interconnect layers 450. Encapsulation proceeds as explained above for FIG. 2A. After encapsulation, the second cover 350 has encapsulated both the second electrical component 310 and the further electrical component 320.

FIG. 3B shows an alternative method for providing the second component cover 350—in this case, the cover 350 is rotationally attached to the first flexible layer 410 as depicted in FIG. 2B.

Figure 4A:
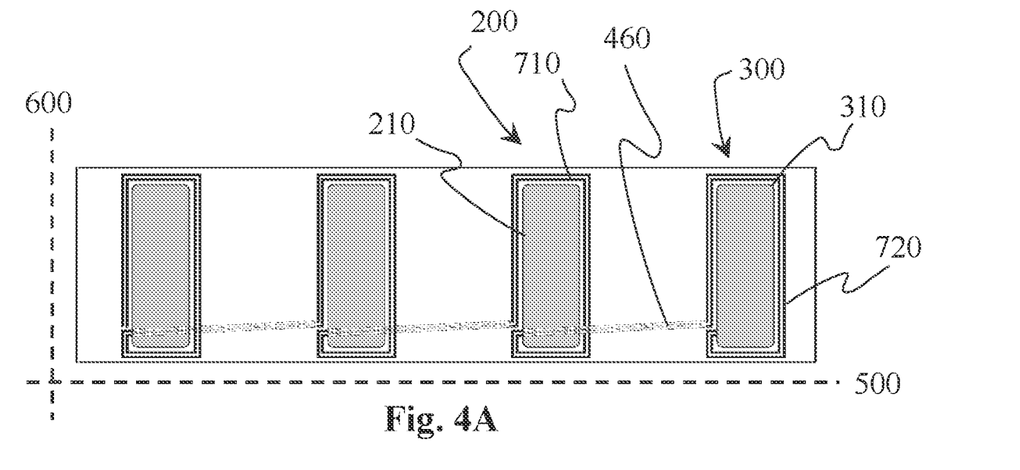
FIGS. 4A and 4B depict a further embodiment of the improved device.
Figure 4B:
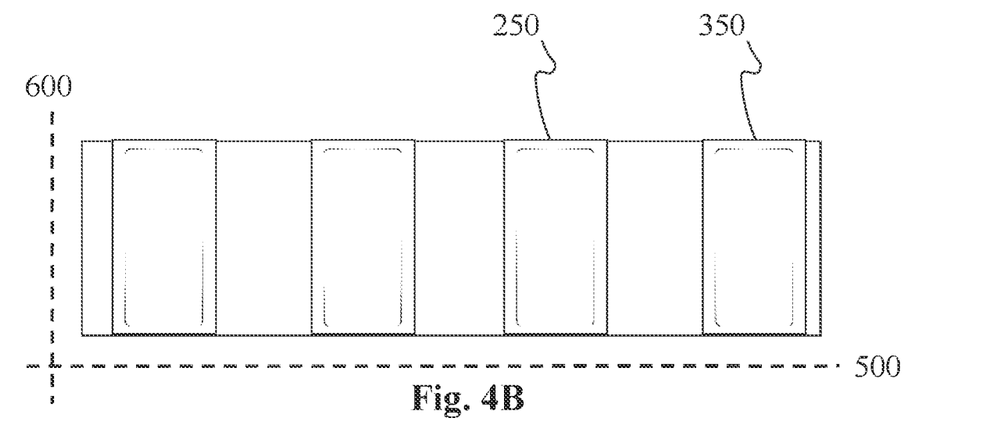

FIG. 3C depicts schematically a longitudinal cross-section showing the bend-points, similar to FIG. 2C. Note that the first 200 and second 300 component positions are relatively flat, and the bending occurs substantially between the first 250 and second 350 covers. The region of maximum bend is the region of highest force/tension in the substrate 410, 450, 470—in this case, the relatively large dimensions along the longitudinal axis 500 means that it is more difficult for the implantable medical device to follow the circular cross-section FIGS. 4A and 4B depict a further embodiment which is very similar to FIG. 2A. An improved implantable device 100 having a plurality of component positions is shown. The first component position 200 comprises the first electrical component 210 on an outer surface of the flexible surface, and which has not yet been encapsulated. At the second component position 300, the second electrical component 310 is provided on an outer surface of the flexible surface. It is also not yet encapsulated.

Both the second position 300 and first position 200 further comprise a sensor—in this case, it is a fluid detector 710, two or more electrical conductors, substantially equidistant over at least part of their extent. In this case, comprising two or more substantially parallel electrical conductors. A similar fluid detector 710 is depicted in FIG. 9B. Typically, the electrical conductor will have a width of between 50 microns (um) and 1 mm, although any suitable size may be used.

The path of the electrical conductors is around at least a part of the perimeter of the one or more encapsulated components 210, 310 at the respective component position 200, 300. The path is selected to be proximate the sealed edge of the respective component cover 250, 350 which represent a likely region for fluid ingress during device operation due to possible defects and/or deteriorations in the sealing.

Advantageously, the electrical conductors cover substantially the whole of the perimeter of the encapsulated component position so that any ingress of fluid is detected quickly. However, a sensor anywhere in the encapsulation may be configured to detect a raised humidity level which typically indicates that some ingress has occurred.

In spite of optimizing the design, materials and processes, a degree of ingress may occur. In addition, particularly when using flexible substrates, defects may occur after a period of time allowing some fluid to penetrate into the component encapsulation. It is therefore particularly advantageous to provide a fluid sensor at one or more component positions 200, 300, within the encapsulation.

Different configurations may be provided—for example, a single component position may comprise a fluid detector and provide the information to one or more other component positions through the interconnection layer 450.

As depicted in FIG. 4A, a further interconnection 460 or further interconnection layer 460 may be provided for sensors, and in particular for a fluid sensor 710.

As depicted in FIG. 4A, both first 200 and second 300 component positions comprise a fluid sensor 710, 720. These fluid sensors are optionally connected in series, so that more than one component position may become aware of an unacceptable degree of ingress in any of the other component positions.

FIG. 4B depicts the improved implantable device of FIG. 4A after encapsulation as described above in relation to FIG. 2.

Figure 9A:
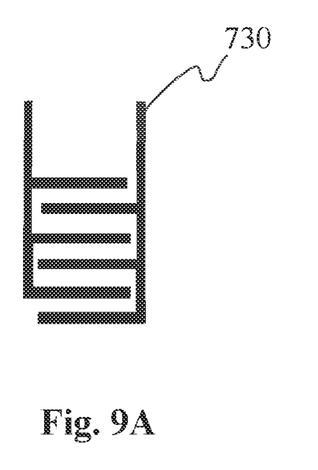
FIGS. 9A & 9B depict embodiments of fluid sensors which may be used in the device.
Figure 9B:
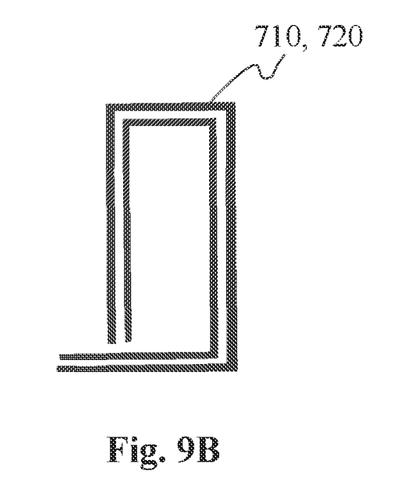

Additionally or alternatively, one or more further fluid sensors 730, such as that depicted in FIG. 9A may be used. These may be comprised within an encapsulated component position 200, 300, or at a further position to measure the implant environment. The sensor depicted in FIG. 9A is of the interlocking comb type, which are available in SMD dimensions—the interlocking conductors are substantially equidistant, and many different dimensions and aspect ratio are possible. However, any similar sensor may also be used.

Figure 8A:
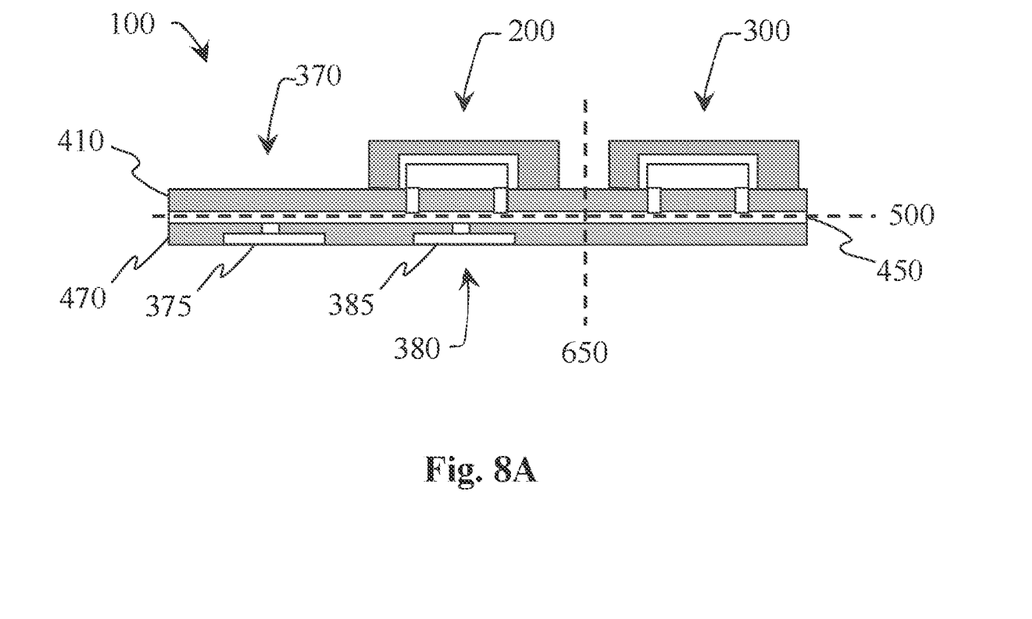
FIGS. 8A and 8B depict the implantable medical device with one or more optional a third electrical components.

As depicted in FIG. 8A, the implantable medical device 100 may optionally further comprise:
  a third electrical component 375 disposed at a third component position 370 disposed further along the longitudinal axis 500 from the first 200 and/or second 300 component position;

the third electrical component 375 being electrically connected with the first 210 and/or second 310 electrical component through the one or more electrical interconnect layers 450;

the third electrical component 375 being a stimulation electrode and/or a sensor.

A stimulation electrode 375 is configured to transmit energy to human or animal tissue. A sensor 375 is configured to detect a presence of an environmental property in human or animal tissue.

Alternatively or additionally, a fourth component 385 may be disposed along the second transverse axis 650 at a fourth component position 380. The fourth component 385 may also be a stimulation electrode 385 and/or a sensor 385.

Alternatively or additionally, a fifth component (not depicted) may be disposed along the first transverse axis 600 at a fifth component position (not depicted). The fifth component may also be a stimulation electrode and/or a sensor.

One or more stimulation electrodes and/or sensor may be provided along the longitudinal axis 500, the first transverse axis 600, the second transverse axis 650 and any combination thereof. The skilled person will realize that such a stimulation electrode and/or sensor is not fully encapsulated, as electrical connection or exposure to the implant environment are required for their function.

Typically with neural-stimulation electrodes, an electrode is provided and configured as a ground electrode—this may be one of the existing electrodes or a further electrodes.

In FIG. 8A, a third component position 370 is depicted, disposed along the longitudinal axis 500. A fourth component position 380 is also depicted, proximate the second component position 200 disposed along the second transverse axis 650.

Figure 8B:
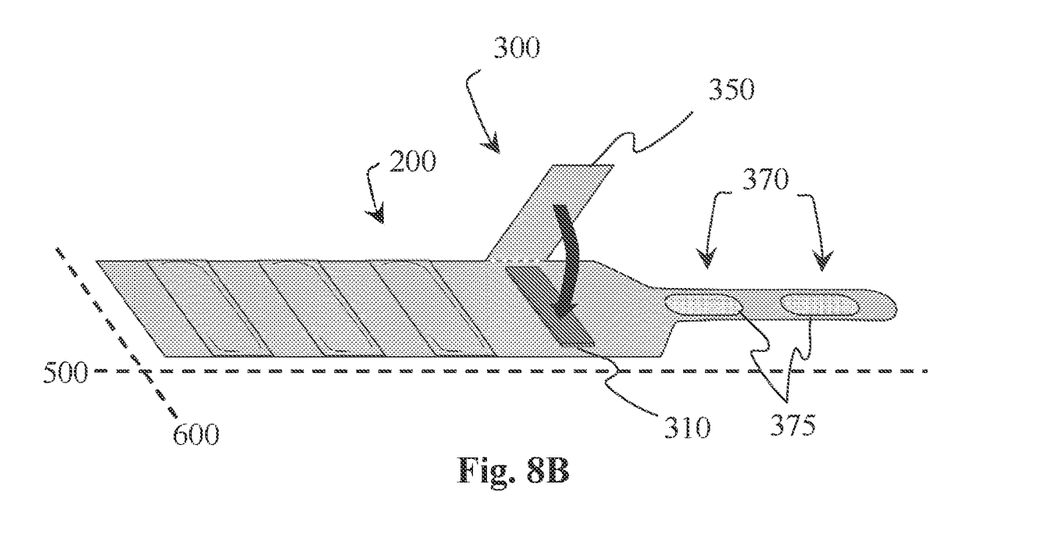

FIG. 8B depicts a similar perspective view of a device 100 to that depicted in FIG. 2B—however, this device further comprises a third component (electrode) 375 at a third component position 370, and a further third component (electrode) 375 at a further third component position 370. The electrodes 375 are configured to be used as neurostimulation electrodes. Although depicted on the "upper" surface, the electrodes 375 may also be configured to be disposed on the "lower" surface of the substrate. In many neurostimulation applications, a plurality of electrodes may be required.

Such a multilayer substrate allows a high degree of customization in sensors and electrodes. For example, allowing direct measurements of parameters relevant for operation, such as humidity, temperature, electrical resistance and electrical activity.

Figure 5:
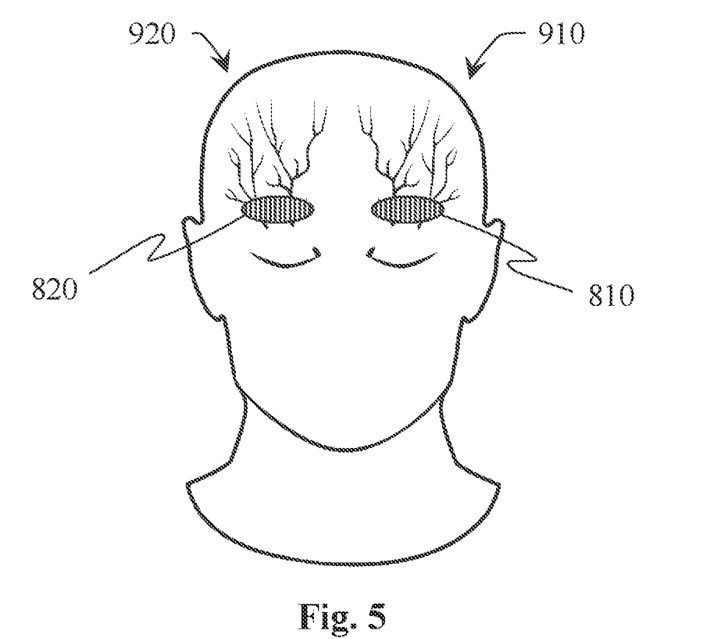
FIG. 5 and FIG. 6 depict examples of nerves that may be stimulated to treat headaches.
Figure 6:
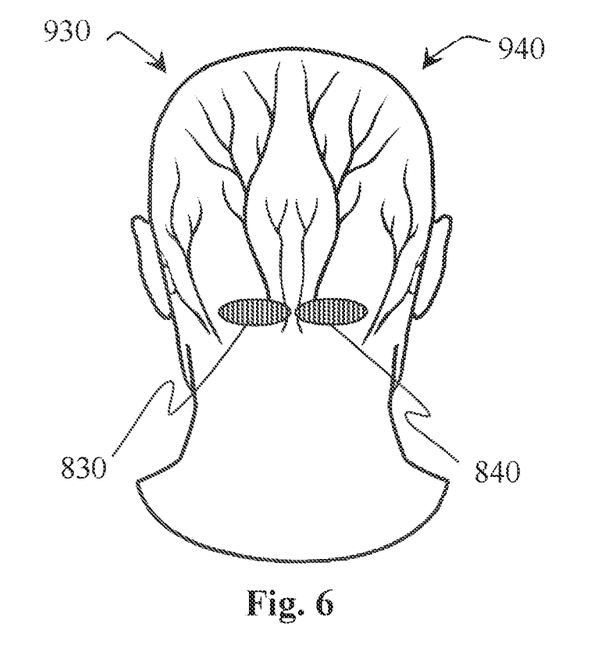

FIG. 5 and FIG. 6 depict examples of nerves that may be stimulated using a suitably configured improved implantable device 100 to provide neurostimulation to treat, for example, headaches or primary headaches. The ability to conform to the curved surfaces of the head and/or skull means that the comfort to the user of the implantable device 100 is increased.

FIG. 5 depicts the left supraorbital nerve 910 and right supraorbital nerve 920 which may be electrically stimulated using a suitably configured device. FIG. 6 depicts the left greater occipital nerve 930 and right greater occipital nerve 940 which may also be electrically stimulated using a suitably configured device.

Depending on the size of the region to be stimulated and the dimensions of the part of the device to be implanted, a suitable location is determined to provide the electrical stimulation required for the treatment. Approximate implant locations for the part of the stimulation device comprising stimulation electrodes are depicted as regions:

location 810 for left supraorbital stimulation and location 820 for right supraorbital stimulation for treating chronic headache such as migraine and cluster.

location 830 for left occipital stimulation and location 840 for right occipital stimulation for treating chronic headache such as migraine, cluster, and occipital neuralgia.

In many cases, these will be the approximate locations 810, 820, 830, 840 for the implantable electrode unit 100.

For each implant location, 810, 820, 830, 840 a separate stimulation device 100 may be used. Where implant locations 810, 820, 830, 840 are close together, or even overlapping a single stimulation device 100 may be configured to stimulate at more than one implant location 810, 820, 830, 840.

A plurality of stimulation devices 100 may be operated separately, simultaneously, sequentially or any combination thereof to provide the required treatment.

Figure 7:
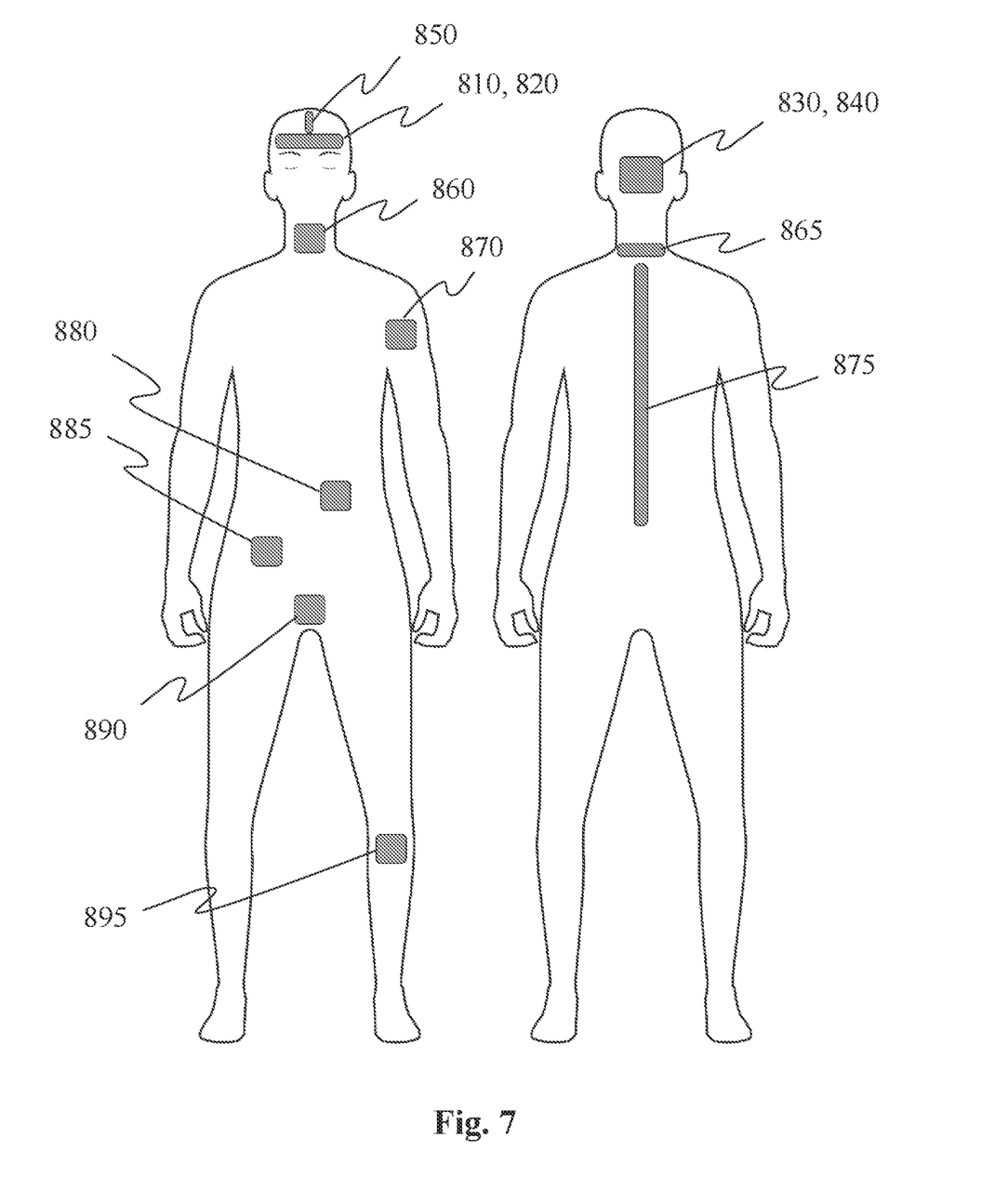
FIG. 7 depicts examples of nerves that may be stimulated for other treatments.

FIG. 7 depict further examples of nerves that may be stimulated using a suitably configured improved implantable device 100 to provide neurostimulation to treat other conditions. As in FIGS. 5 and 6, the ability to conform to the curved surfaces in these locations that the comfort to the user of the implantable device 100 is increased. The locations depicted in FIG. 5 and FIG. 6 (810, 820, 830, 840) are also depicted in FIG. 7.

Depending on the size of the region to be stimulated and the dimensions of the part of the device to be implanted, a suitable location is determined to provide the electrical stimulation required for the treatment. Approximate implant locations for the part of the stimulation device comprising stimulation electrodes are depicted as regions:

location 810 for cortical stimulation for treating epilepsy;

location 850 for deep brain stimulation for tremor control treatment in Parkinson's disease patients; treating dystonia, obesity, essential tremor, depression, epilepsy, obsessive compulsive disorder, Alzheimer's, anxiety, bulimia, tinnitus, traumatic brain injury, Tourette's, sleep disorders, autism, bipolar; and stroke recovery location 860 for vagus nerve stimulation for treating epilepsy, depression, anxiety, bulimia, obesity, tinnitus, obsessive compulsive disorder and heart failure;

location 860 for carotid artery or carotid sinus stimulation for treating hypertension;

location 860 for hypoglossal & phrenic nerve stimulation for treating sleep apnea;

location 865 for cerebral spinal cord stimulation for treating chronic neck pain;

location 870 for peripheral nerve stimulation for treating limb pain, migraines, extremity pain;

location 875 for spinal cord stimulation for treating chronic lower back pain, angina, asthma, pain in general;

location 880 for gastric stimulation for treatment of obesity, bulimia, interstitial cystitis;

location 885 for sacral & pudendal nerve stimulation for treatment of interstitial cystitis;

location 885 for sacral nerve stimulation for treatment of urinary incontinence, fecal incontinence;

location 890 for sacral neuromodulation for bladder control treatment; and location 895 for fibular nerve stimulation for treating gait or footdrop.

The one or more electrical components 210, 310, 320 may comprise: an active component, a passive component, an electronic component, an integrated circuit (IC), an application-specific integrated circuit (ASIC), a field-programmable gate array (FPGA), an analog component, a digital component, a surface-mount device (SMD), a through-hole package, a chip carrier, a pin grid array, a fat package, a small outline package, a chip scale package, a ball grid array, a small-pin-count package, a flexible silicon device, a thin-film transistor (TFT), and any combination thereof.

The first electrical component 210 may be a discrete component such as: an active component, a passive component, an electronic component, an analog component, a digital component, a surface-mount device SMD, a flexible silicon device, a thin-film transistor TFT, and any combination thereof.

Additionally or alternatively, the second electrical component 310, 320 may be an integrated circuit component, such as: an active component, an electronic component, an integrated circuit IC, an application-specific integrated circuit ASIC, a field-programmable gate array FPGA, an analog component, a digital component, a surface-mount device SMD, a through-hole package, a chip carrier, a pin grid array, a flat package, a small outline package, a chip scale package, a ball grid array, a small-pin-count package, and any combination thereof The one or more electrical components 210, 310, 320 may comprise a component configured and arranged to: resist, store charge, induct, sense, stimulate, amplify, process data, detect, compare, switch, time, store data, count, oscillate, perform logic, add, generate stimulation pulses, and any combination thereof.

Methods described herein should not be understood to prescribe a fixed order of performing the method steps described therein. Rather the method steps may be performed in any order that is practicable.

Although the present invention has been described in connection with specific exemplary embodiments, it should be understood that various changes, substitutions, and alterations apparent to those skilled in the art can be made to the disclosed embodiments without departing from the spirit and scope of the invention as set forth in the appended claims.

For example, an implantable medical device 100 according to the invention may comprise:
- a flexible substrate having one or more electrical interconnect layers 450 interposed between a first flexible substrate layer 410 and a second flexible substrate layer 470;
- a first electrical component 210 disposed at a first component position 200;
- a second electrical component 310 disposed at a second component position 300, the first 300 and second 400 component positions being disposed along a longitudinal axis 500;
- the first electrical component 210 being electrically connected with the second electrical component 310 through the one or more electrical interconnect layers 450;
- a first component cover 250, configured and arranged to encapsulate the first component 210 and to resist the ingress of fluids from a human or animal body into the first component position 200;
- a second component cover 350, configured and arranged to separately encapsulate the second component 310 and to resist the ingress of fluids from a human or animal body into the second component position 300;

wherein the flexible substrate is further configured and arranged to allow a relative change in disposition between the first component cover 250 and the second component cover 350;
the first electrical component 210 being a discrete electrical component; and
the second electrical component 310 being an integrated circuit.

REFERENCE NUMBERS USED IN DRAWINGS

100 an improved implantable medical device
200 a first component position
210 a first electrical component
250 a first component cover
300 a second component position
310 a second electrical component
320 a further electrical component
350 a second component cover
370 a third component position (longitudinal)
375 a third electrical component (longitudinal)
380 a fourth component position (transverse)
385 a fourth electrical component (transverse)
410 first flexible substrate layer
450 one or more electrical interconnect layers
460 further electrical interconnect layer
470 second flexible substrate layer
500 a longitudinal axis
600 a first transverse axis
650 a second transverse axis
710 a first fluid sensor
720 a second fluid sensor
730 a further fluid sensor
810 location for left supraorbital nerve or cortical stimulation
820 location for right supraorbital stimulation
830 location for left occipital nerve stimulation
840 location for right occipital nerve stimulation
850 location for deep brain stimulation
860 location for vagus nerve, carotid artery, carotid sinus, phrenic nerve or hypoglossal stimulation
865 location for cerebral spinal cord stimulation
870 location for peripheral nerve stimulation
875 location for spinal cord stimulation
880 location for gastric stimulation
885 location for sacral & pudendal nerve stimulation
890 location for sacral neuromodulation
895 location for fibular nerve stimulation
930 left greater occipital nerve
940 right greater occipital nerve

The invention claimed is:
1. An implantable medical device, comprising:
a flexible substrate having one or more electrical interconnect layers interposed between a first flexible substrate layer and a second flexible substrate layer;
a first electrical component disposed at a first component position;
a second electrical component disposed at a second component position, the first and second component positions being disposed and separated along a longitudinal axis;
the first electrical component being electrically connected with the second electrical component through the one or more electrical interconnect layers;

a first component cover, configured and arranged to encapsulate the first component and to resist the ingress of fluids from a human or animal body into the first component position;
a second component cover, configured and arranged to separately encapsulate the second component and to resist the ingress of fluids from a human or animal body into the second component position;
wherein the flexible substrate is further configured and arranged to allow a relative change in disposition between the first component cover and the second component cover;
the device further comprising:
a stimulation electrode, configured to transmit energy to human or animal tissue, disposed at a third component position further along the longitudinal axis from the first and/or second component positions;
the stimulation electrode being electrically connected with the first and/or second electrical component through the one or more electrical interconnect layers.

2. The device according to claim 1, wherein the change in disposition comprises:
a change in separation along the longitudinal axis between the first component cover and the second component cover; and/or
a change in rotation about a transverse axis disposed between the first component cover and the second component cover, the transverse axis being substantially perpendicular to the longitudinal axis; and/or
a change in rotation about the longitudinal axis.

3. The device of according to claim 1, wherein the device comprises a Liquid Crystal Polymer LCP and/or a Polyimide in:
the first flexible substrate layer; and/or
the second flexible substrate layer; and/or
the first component cover; and/or
the second component cover.

4. The device according to claim 1, wherein
the first electrical component is an analog component and
the second electrical component is a digital component.

5. The device according to claim 1, wherein
the first electrical component is a discrete electrical component and
the second electrical component is an integrated circuit.

6. The device according to claim 1, wherein the first component position and/or second component position further comprises a fluid detector, the fluid detector encapsulated by the first component cover or the second component cover, respectively.

7. The device according to claim 6, wherein the fluid detector comprises two or more electrical conductors, disposed around at least a part of the perimeter of the encapsulated component at the respective component position.

8. The device according to claim 7, wherein the two or more electrical conductors are disposed around substantially the whole of the perimeter of the encapsulated component at the respective component position.

9. The device according to claim 6, wherein a first fluid detector at the first component position is electrically connected to a second fluid detector at the second component position through an interconnection.

10. The device according to claim 6, wherein the fluid detector is comprised in the first component position and provides information to the second component position through an interconnection.

11. The device according to claim 1, wherein the first electrical component and/or second electrical component have a cross-sectional shape in a plane approximately parallel to a plane comprising the first substrate layer, the shape being circular, oval, elliptical, square, rectangular, or trapezoidal.

12. The device according to claim 1, wherein the first component cover and/or second component cover have a cross-sectional shape in a plane approximately parallel to a plane comprising the first substrate layer, the shape being circular, oval, elliptical, square, rectangular, or trapezoidal.

13. The device according to claim 1, wherein the first electrical component and/or second electrical component have substantially larger dimensions along a transverse axis than along the longitudinal axis.

14. The device according to claim 1, wherein the first component cover and/or second component cover have substantially larger dimensions along a transverse axis than along the longitudinal axis.

15. The device according to claim 1, wherein the first component position and/or second component position comprises a plurality of electrical components, electrically connected to each other with the one or more electrical interconnect layers, and encapsulated by the first component cover or the second component cover, respectively.

16. The device according to claim 1, wherein the one or more electrical components are selected from the group consisting of: an active component, a passive component, an electronic component, an integrated circuit IC, an application-specific integrated circuit ASIC, a field-programmable gate array FPGA, an analog component, a digital component, a surface-mount device SMD, a through-hole package, a chip carrier, a pin grid array, a fat package, a small outline package, a chip scale package, a ball grid array, a small-pin-count package, a flexible silicon device, a thin-film transistor TFT, and combinations thereof.

17. The device according to claim 1, wherein the first electrical component is selected from the group consisting of: an active component, a passive component, an electronic component, an analog component, a digital component, a surface-mount device SMD, a flexible silicon device, a thin-film transistor TFT, and combinations thereof.

18. The device according to claim 1, wherein the second electrical component is selected from the group consisting of: an active component, an electronic component, an integrated circuit IC, an application-specific integrated circuit ASIC, a field-programmable gate array FPGA, an analog component, a digital component, a surface-mount device SMD, a through-hole package, a chip carrier, a pin grid array, a flat package, a small outline package, a chip scale package, a ball grid array, a small-pin-count package, and combinations thereof.

19. The device according to claim 1, wherein the one or more electrical components comprises a component configured and arranged to perform a function selected from the group consisting of: resist, store charge, induct, sense, stimulate, amplify, process data, detect, compare, switch, time, store data, count, oscillate, perform logic, add, generate stimulation pulses, and combinations thereof.

20. The device according to claim 1, wherein the first component cover fully encapsulates the first component and the second component cover fully encapsulates the second component.

21. The device according to claim 1, wherein the first component cover is larger than the first component such that a distance of at least 300 microns exists between one or more sides of the first component and the first component cover, and/or the second component cover is larger than the second component such that a distance of at least 300 microns exists between one or more sides of the second component and the second component cover.

22. The device according to claim 1, wherein the first and second electrical components are each configured to control electron flow.

23. The device according to claim 1, wherein the first and second component covers do not touch or overlap.

* * * * *